United States Patent [19]

Glass

[11] Patent Number: 5,858,186
[45] Date of Patent: Jan. 12, 1999

[54] UREA BIOSENSOR FOR HEMODIALYSIS MONITORING

[75] Inventor: Robert S. Glass, Livermore, Calif.

[73] Assignee: The Regents of the University of California, Oakland, Calif.

[21] Appl. No.: 777,682

[22] Filed: Dec. 20, 1996

[51] Int. Cl.[6] .................................................. G01N 27/26
[52] U.S. Cl. .................... 204/403; 204/418; 204/433; 435/287.1; 435/289.1; 435/817
[58] Field of Search .................................... 204/403, 433, 204/418; 435/817, 287.1, 289.1

[56] References Cited

U.S. PATENT DOCUMENTS

| | | | |
|---|---|---|---|
| 3,930,957 | 1/1976 | Cummings et al. | 195/103.5 R |
| 4,225,410 | 9/1980 | Pace | 204/195 R |
| 4,244,787 | 1/1981 | Klein et al. | 204/1 T |
| 4,452,682 | 6/1984 | Takata et al. | 204/403 |
| 5,110,441 | 5/1992 | Kinlen et al. | 204/418 |
| 5,120,421 | 6/1992 | Glass et al. | 204/406 |
| 5,296,125 | 3/1994 | Glass et al. | 204/153.21 |
| 5,308,315 | 5/1994 | Khuri et al. | 604/4 |
| 5,397,451 | 3/1995 | Senda et al. | 204/418 |
| 5,480,534 | 1/1996 | Kato et al. | 204/433 |

FOREIGN PATENT DOCUMENTS

| | | |
|---|---|---|
| 92104494 | 3/1992 | European Pat. Off. . |
| WO94/08641 | 4/1994 | WIPO . |

OTHER PUBLICATIONS

Pier Giorgio Pietta et al., "Assay of Urea by Immobilized Urease Coupled To A Differential pH–Meter", Annals New York Academy of Sciences, pp. 257–263.

R.M. Ianniello et al., Analytica Chimica Acta, 146, (1983) 249–253.

N.J. Szuminsky et al., Biotechnology and Bioengineering, vol. XXVI, pp. 642–645 (1984).

R. Tor et al., Anal. Chemi., vol. 58, No. 6, May 1986, pp. 1042–1052.

M. Przybyt et al., Analytica Chimica Acta, 237 (1990) pp. 399–404.

M. Przybyt et al., Analytica Chimica Acta, 239 (1990) pp. 269–276.

R. Konchi et al., Analytica Chimica Acta, 257 (1992) pp. 67–72.

Glab et al, Metal–Metal Oxide and Metal Oxide Electrodes as pH sensors, vol. 21, Issue 1, 1989, pp. 29–47.

Ianniello et al, Urea sensor based on iridium dioxide electrodes with immobilized urease, anal. chimica acta, 146 (1983) 249–253.

*Primary Examiner*—Bruce F. Bell
*Attorney, Agent, or Firm*—L. E. Carnahan

[57] ABSTRACT

An electrochemical sensor capable of detecting and quantifying urea in fluids resulting from hemodialysis procedures. The sensor is based upon measurement of the pH change produced in an aqueous environment by the products of the enzyme-catalyzed hydrolysis of urea. The sensor may be fabricated using methods amenable to mass fabrication, resulting in low-cost sensors and thus providing the potential for disposable use. In a typical application, the sensor could be used in treatment centers, in conjunction with an appropriate electronics/computer system, in order to determine the hemodialysis endpoint. The sensor can also be utilized to allow at-home testing to determine if dialysis was necessary. Such a home monitor is similar, in principle, to devices used for blood glucose testing by diabetics, and would require a blood droplet sample by using a finger prick.

20 Claims, 4 Drawing Sheets

UREA BIOSENSOR FOR HEMODIALYSIS MONITORING

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electrochemical sensors, particularly to sensors for detecting urea in body fluids, and more particularly to a sensor capable of detecting and quantifying urea in fluids resulting from hemodialysis procedures.

There are currently more than 300,000 people with end-stage renal disease in the United States who require regular hemodialysis. Urea is generally accepted to be the best marker for evaluating the level of uremic toxins. Dialysis procedures are therefore aimed at reduction of urea in the blood stream. Currently, most dialysis clinics use the simple index of time of dialysis to determine the adequacy of dialysis. Blood draws (or other methods of obtaining blood samples) to accurately measure the level of urea in blood are often done infrequently to lower cost. The frequency of this measurement, which requires the use of clinical laboratories, varies from facility to facility. Turnaround time for these samples can be quite long, and often the patient must be recalled for further dialysis if the percentage reduction of urea in the blood is not sufficient. In the absence of a blood check, the use of time of dialysis alone as a measure of completion, especially if hemodialysis is not carried out long enough, can clearly lead to morbidity and mortality.

Substantial effort has been directed toward development of procedures for dialysis and blood urea monitoring, and various mechanical and sensor systems and methods have been developed, as exemplified by various patents including International Patent WO94/08641, April 1994, to P. Keshaviah et al.; European Patent EP504772, November 1992, to B. Skerratt; and U.S. Pat. No. 4,452,682 issued June 1984 to Y. N. Takata et al.; No. 3,930,957 issued January 1976 to J. P. Cummings et al.; No. 4,225,410 issued September 1980 to S. J. Pace; No. 5,308,315 issued May 1994 to R. N. Khuri et al.; and No. 4,244,787 issued January 1981 to E. Klein et al. In addition, a sensor has been recently developed which deals with dialysis monitoring, as described and claimed in copending U.S. application Ser. No. 08/517,011, filed Aug. 18, 1995, entitled "Chemiresistor Urea Sensor", and assigned to the same assignee.

Also, there is substantial published literature on urea sensors which deal with the use of a glass pH electrode (conventional liquid-filled glass tube), see R. Tor et al., Anal. Chem. 58, 1042–1046 (1986); R. Koncki et al., Anal. Chim. Acta. 257, 67–72 (1992); and P. Pietta et al., Ann. NY Acad. Sci., Vol. 672, 257 (1992). Also, publications have dealt with the use of metal/metal oxide systems as a basis for measurement of pH changes to determine urea concentration in various fluids, see N. Szuminsky et al., Biotech. and Bioeng., Vol. XXXVI, 642–645 (1984); R. Ianniello et al., Anal. Chim. Acta., 146, 249–252 (1983); M. Przybyt et al., Anal. Chim. Acta., 239, 269–276 (1990); and M. Przybyt et al., Anal. Chim. Acta., 237, 399–404 (1990). The above-referenced Ianniello et al. article in particular deals with the use of iridium oxide as a pH-sensitive material.

All of these prior devices rely upon the encapsulation of the enzyme urease, which catalyzes the hydrolysis of urea to yield products which result in the pH changes, which are then detected and related to the original urea concentration in the monitored fluid. Encapsulation using bovine serum albumin, cross-linked using glutaraldehyde has been previously discussed (e.g. above-reference N. Szuminsky et al., article).

Thin film deposition for sensor fabrication has been previously utilized for environmental sensors, see U.S. Pat. No. 5,120,421 issued Jun. 9, 1992; and No. 5,296,125 issued Mar. 22, 1994, each in the name of R. S. Glass et al.

It has long been desired to have a sensor which could monitor the progress of the dialysis procedure in "real-time", thereby assuring that the procedure was complete and obviating the need for using clinical laboratories and the necessity for patient recall. The most convenient fluid to monitor is the dialysate, which is the capturing medium for blood contaminants during the hemodialysis process. Monitoring in dialysate would result in a completely in vitro procedure. By use of an appropriate sensor arrangement, the dialysate could be continuously or intermittently monitored at the point-of-care. A further enhancement of this general principle is a home monitor, which would allow at-home testing to determine if dialysis was necessary. Such a home monitor could be similar, in principle, to devices used for blood glucose testing by diabetics. Such a device could require a mere blood droplet sample provided by a finger prick.

The above-referenced needs have been satisfied by the present invention which involves an electrochemical sensor whereby the dialysate can be continuously or intermittently monitored, and can be incorporated into a home monitor. The sensing element is used with an appropriate electronics package and can be tied to a computerized system which would contain individual patient case histories, to determine the dialysis end points. The sensor of this invention is based upon measurement of the pH change produced in an aqueous environment by the products of the enzyme-catalyzed hydrolysis of urea. The sensor element consists of a solid-state pH-sensitive material, such as $IrO_2$, coated with the enzyme urease.

SUMMARY OF THE INVENTION

It is an object of the present invention to provide a sensor for hemodialysis monitoring.

A further object of the invention is to provide a urea biosensor for hemodialysis monitoring using a solid-state pH electrode.

A further object of the invention is to provide a method of fabricating a sensor for hemodialysis monitoring which can be utilized for mass fabrication operations.

Another object of the invention is to provide a sensor which can monitor the progress of the dialysis procedure in "real-time".

Another object of the invention is to provide a sensor which enables continuous or intermittent monitoring during the hemodialysis process.

Another object of the invention is to provide a urea biosensor for hemodialysis monitoring, which can be utilized for at-home testing to determine if dialysis is necessary.

Another object of the invention is to provide a method for fabricating a sensor element for urea detection which involves depositing a solid-state pH-sensitive material followed by a coating containing the enzyme urease.

Other objects and advantages will become apparent from the following description and accompanying drawings.

Basically, the invention involved a urea biosensor for hemodialysis monitoring using a solid-state pH electrode, and to the method for fabricating same. The sensor element for urea detection consists of a solid-state pH-sensitive material coated with the enzyme urease. The sensor enables continuous or intermittent monitoring at the point-of-care, or can be utilized as a home monitor to determine if one suffering with end-stage renal disease need go to a point-of-care for dialysis. The sensor detects pH changes produced as a result of the urease-catalyzed hydrolysis of urea; the products of this reaction, ammonia and carbon dioxide, by virtue of their pKa's will change the pH of an unbuffered, or inadequately buffered aqueous medium. It has been found that some oxides possess pH-dependent electrochemical equilibria, making them candidates for application as pH sensors and electrochromics, one of which is iridium oxide ($IrO_2$). The sensor element fabrication method basically involves depositing a thin film or layer of a selected material, such as iridium (Ir) on a substrate, such as alumina, silicon, glass, or KAPTON followed by depositing a thin film or layer of a pH-sensitive material, such as $IrO_2$, on a portion of the Ir film or layer. Where needed, a thin adhesion layer or film, such as titanium, can be deposited on the substrate prior to the layer of first selected material (Ir).

The sensor of this invention can be utilized wherever there is a need to monitor patients who require dialysis, be it for home testing or for at a point-of-care facility.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention is directed to an electrochemical sensor capable of detecting and quantifying urea in body fluids, particularly in fluids resulting from hemodialysis procedures, and to the fabrication method thereof. The sensor is based upon measurement of the pH change produced in an aqueous environment by the products of the enzyme-catalyzed hydrolysis of urea. The most convenient body fluid to monitor is the dialysate, which is the capturing medium for blood contaminants during the hemodialysis process. By use of the sensor of this invention the dialysate can be continuously or intermittently monitored at the point-of-care facility. The sensor of this invention also enables at-home testing to determine if dialysis is necessary. The sensor is utilized with an electronic package, and can be incorporated into a computerized system which would contain individual patient case histories, to determine the patient-specific dialysis end-points.

The sensor element of this invention includes a solid-state pH-sensitive material coated with a material containing the enzyme urease. Urease of different enzymatic activities can be used, for example, 74,000 units/g. The sensor detects pH changes produced as a result of the urease-catalyzed hydrolysis of urea:

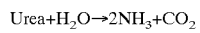

$$Urea + H_2O \rightarrow 2NH_3 + CO_2$$

The products of this reaction, ammonia and carbon dioxide, by virtue of their pKa's will change the pH of an unbuffered, or inadequately buffered aqueous medium.

As pointed out above, the most well-known device for measuring pH is the common glass pH electrode, which measures pH through potentials induced across a glass membrane. A glass electrode could be coated with urease and used to detect urea. However, such a glass electrode system is fragile, would require maintenance, is relatively expensive, and is not usually thought of as a disposable instrument. It has been found that oxides possess pH-dependent electrochemical equilibria, making them candidates for application as pH sensors and electrochromics.

The present invention utilizes a pH-sensitive oxide, iridium oxide ($IrO_2$), deposited on a substrate, such as alumina or an insulated silicon wafer, with a film or coating of a urease-containing material.

Figure 1:
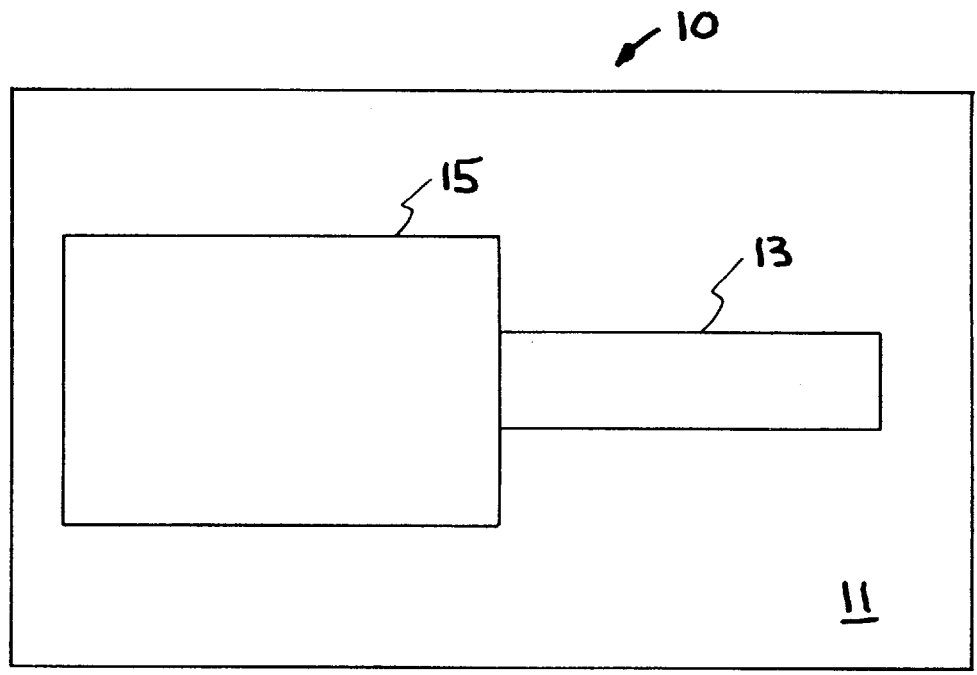
FIG. 1 is a view of a sensor element including an urease coating in accordance with the present invention.
Figure 2:
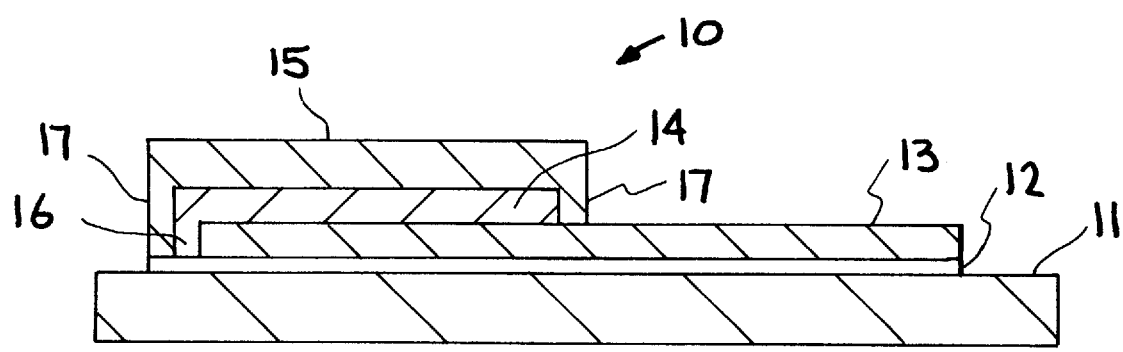
FIG. 2 is a cross-sectional view of the sensor element of FIG. 1 which more clearly illustrates the urease coating and other layers of the sensor element.

Referring now to FIGS. 1 and 2, which illustrate an embodiment of a urea biosensor element for hemodialysis monitoring using a solid-state pH electrode, made in accordance with the present invention. As shown, the sensor element generally indicated at 10 comprises a substrate 11, a thin film of adhesion material 12, a layer of metal 13 which serves both an electrochemical use and as a contact for measuring equipment, a layer or film 14 of a pH-sensitive oxide deposited on a portion of layer 13 and a film or coating 15 of material containing urease deposited on the oxide layer 14. Note as shown in FIGS. 1 and 2, in this embodiment the oxide layer 14 is wider than the metal layer 13 and extends over one end of layer 13 as indicated at 16. Also, the coating 15 covers the top surface of the layer 14 and the side surfaces as indicated at 17. In this embodiment, the substrate 11 can have any desired thickness, preferably 100 $\mu$m to 1 mm, any desired width, preferably 2 mm to 10 mm, and any desired length, preferably 1.5 cm to 5 cm, and may be composed of alumina, insulated silicon, plastic, and glass, for example; the adhesion layer 12 has a thickness of about 200 Å, and may be composed of titanium, chromium or niobium, depending on the composition of the substrate and/metal layer. However, the adhesion layer 12 can be omitted depending on the composition of the substrate and metal layer. The metal layer 13 is composed of iridium having a preferable thickness of 2000 to 4000 Å, width of preferably 1 to 5 mm and length of 1 to 3 cm, noting that the width and length are less than that of substrate 11. Metal layer 13 may also be composed of titanium, platinum, ruthenium, osmium, tantalum, or tungsten. The film or layer 14 is composed of iridium oxide ($IrO_2$) has a preferable thickness of 2000–4000 Å, a width of 1.5 to 6 mm and length of 0.5 to 1.5 cm, being shorter and wider than metal layer 13.

While $IrO_2$ is the preferable material, other pH-sensitive oxides may be used, including: $TiO_2$, $RuO_2$, and $PtO_2$, $OSO_2$, $Ta_2O_5$, or $WO_3$. The end 16 of layer 14 which extends over the end of metal layer 13 has a thickness of 500 to 2000 Å. Note that since the $IrO_2$ layer 14 extends beyond the width of iridium layer 13, that portion of the oxide layer may have the same thickness as the portion located over the end of layer 13. Coating or film 15 may be composed of a cross-linked bovine serum albumin (BSA) film containing urease (e.g. 74,000 unit/g), having a preferable thickness of 1 to 100 µm on the top surface over the $IrO_2$ film 14, and a similar wall thickness on the side surfaces 17.

Urease can either be physically entrapped or covalently bound within the coating material. The coating material containing the urease may be a polymer, such as poly (vinyl alcohol), and copolymers of poly (vinyl alcohol), polypyrrole, polyvinyl pyridine, polyalkylthiophenes, or sol-gels, or bovine serum albumin (BSA) cross-linked with glutaraldehyde, or contain something like Ab-antiurease, to which urease could be covalently attached.

Figure 3:
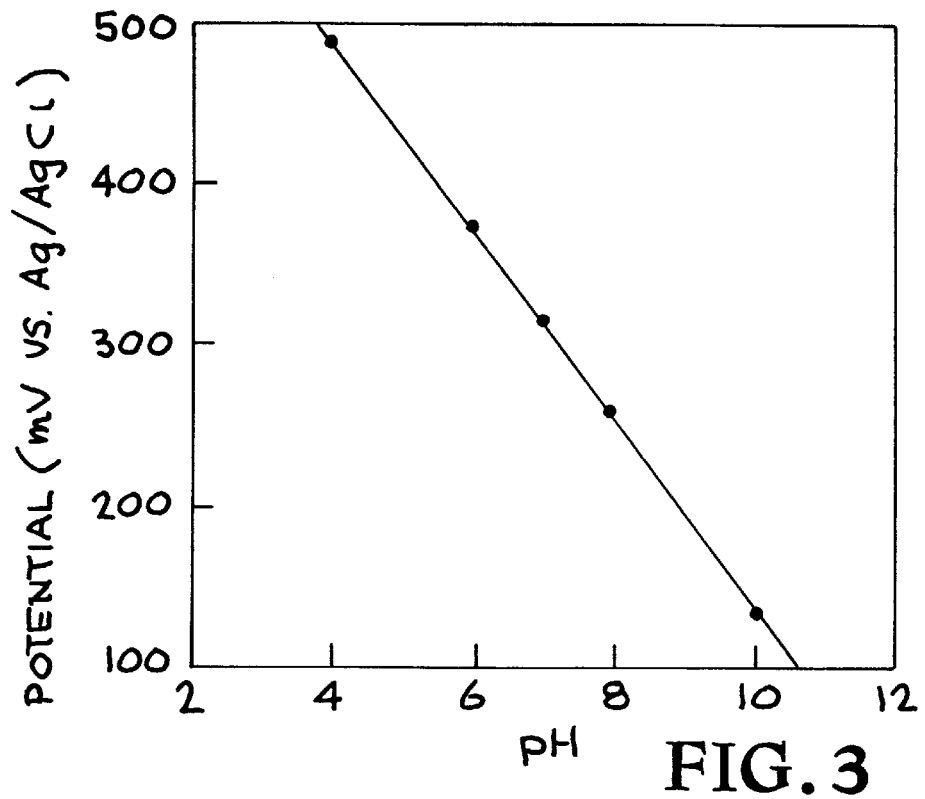
FIG. 3 graphically shows the pH response in standard buffers for a typical sputtered thin iridium oxide ($IrO_2$) film (response of device of FIG. 2 without the urease coating).
Figure 4:
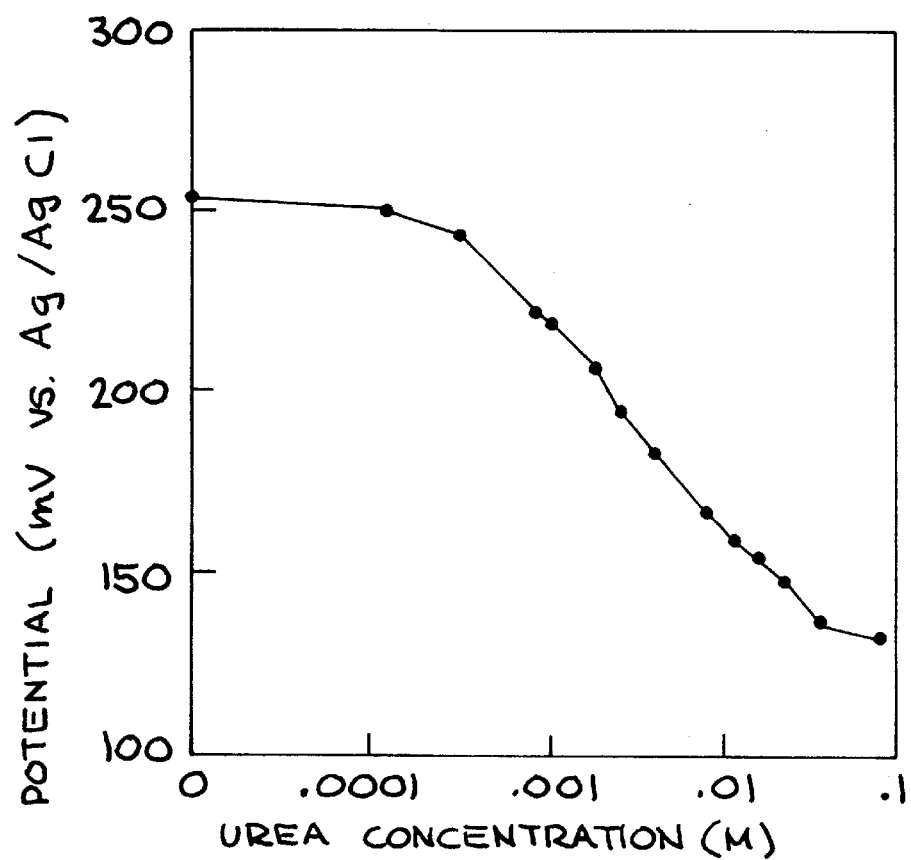
FIG. 4 graphically illustrates the response of a urea sensor of the invention to changes in urea concentration in dialysate fluid.

The pH response (potential measured against a reference electrode, such as silver/silver chloride), as a function of pH for a typical sputtered thin iridium oxide ($IrO_2$) film in standard buffers is shown in FIG. 3. The sensor illustrated in FIGS. 1–2 has been experimentally verified. Example data of response of urea sensor to changes in urea in dialysate fluid is shown in FIG. 4. The urease-containing coating was a cross-linked BSA film containing urease (74,000 unit/g). These tests showed that the sensor has a linear response over the medically important range of interest.

The sensor element of FIGS. 1 and 2 may be fabricated as follows:

1. Select an appropriate substrate.
2. Deposit a thin (500 Å) adhesion layer, such as titanium, on the selected surface of substrate by dc magnetron sputtering a titanium target at 100 W in a 7–10 mTorr argon atmosphere. The titanium is deposited through a molybdenum mask placed on the substrate. The mask has an opening of defined geometry.
3. Deposit a layer of metal, such as iridium, to a thickness of 2000 to 4000 Å on the adhesive layer by dc magnetron sputtering an iridium target at 37 W in a 10–16 mTorr argon atmosphere. The iridium is deposited through an appropriate mask similar to the method used to deposit titanium.
4. Deposit a layer of a pH-sensitive oxide, such as iridium oxide ($IrO_2$) to a thickness of 2000–4000 Å on a section of metal layer and such that it extends over the sides and one end of the metal layer by sputter-deposition of an iridium target at 20 W in 16 mTorr oxygen using a target of pure iridium and a dc magnetron type sputter source.
5. Depositing a layer of urease containing material, such as cross-linked BSA containing urease, to a thickness of 1 to 100 µm over the top and side surfaces of the pH-sensitive oxide layer by applying appropriate solutions and treating. By way of example, a solution of 5000 units/ml of urease was prepared by mixing 6.757 mg of urease (74,000 units/g) with 15 mg bovine serum albumin (BSA) in 0.1 ml of 34 mmol/l phosphate buffer (pH=6.6). Using a micropipette, 1 µl of this solution is coated onto the iridium oxide film portion of the sensor. This is followed by spraying the coated sensor with a 25% solution (in water) of glutaraldehyde to promote crosslinking. Alternative concentrations of urease may also be used in the coating solution, for example, five times more concentrated using a more active enzyme (e.g. 870,000 units/g). The active enzyme range may be 25,000 to 1,000,000 units/g. In addition, other methods of coating may be used. For instance, the BSA solution can be micropipetted followed by micropipetting a solution of gludaraldehyde. Alternatively, the BSA and glutaraldehyde can be mixed together then coated onto the sensor surface.
6. Depending on the composition of the substrate and the metal layer, the adhesion layer may be omitted.

The urea sensor illustrated in FIGS. 1 and 2 is "miacroscopic". That is, with dimensions greater than 100 $\mu m^2$. There may be intrinsic advantages in using an array of microscopic sensors. Namely, immunity to changes in flow in the sampled system. Each iridium oxide sensor in the array would have micron dimensions, for example, disks of 10 µm diameter or less, defining an electrode of an area less than 100 $\mu m^2$. Prior patents (U.S. Pat. No. 5,120,421 and No. 5,296,125) have taught how to manufacture such an array, and the sensors in the array would be jointly accessible. The array could be coated with the BSA and glutaraldehyde solutions as described above.

The above-described sensor element would be used with an instrumentation package capable of measuring the sensor response over time. In its simplest form, this would consist of a voltmeter interfaced to a computer to automate data collection, storage, analysis, and display. Appropriate software would be needed. The computer would be supplied with the appropriate patient-specific profiles in order to determine dialysis end-points. FIGS. 5A–5B and 6A–6C illustrate systems in which the sensor element of FIGS. 1–2 may be utilized.

Figure 5A:
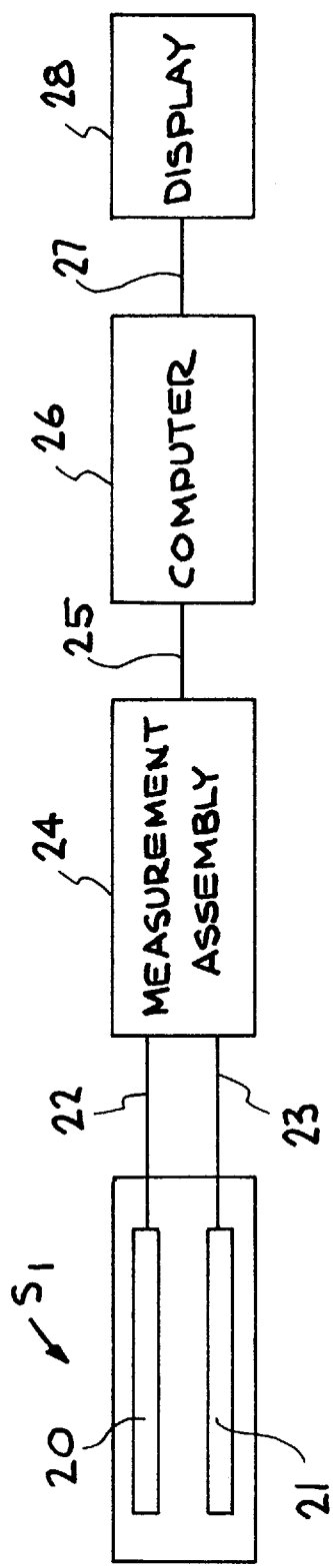
FIG. 5A illustrates a urea sensor, made in accordance with the present invention, used with a reference electrode and interfaced with measurement equipment and computer system in order to determine the hemodialysis end point.
Figure 5B:
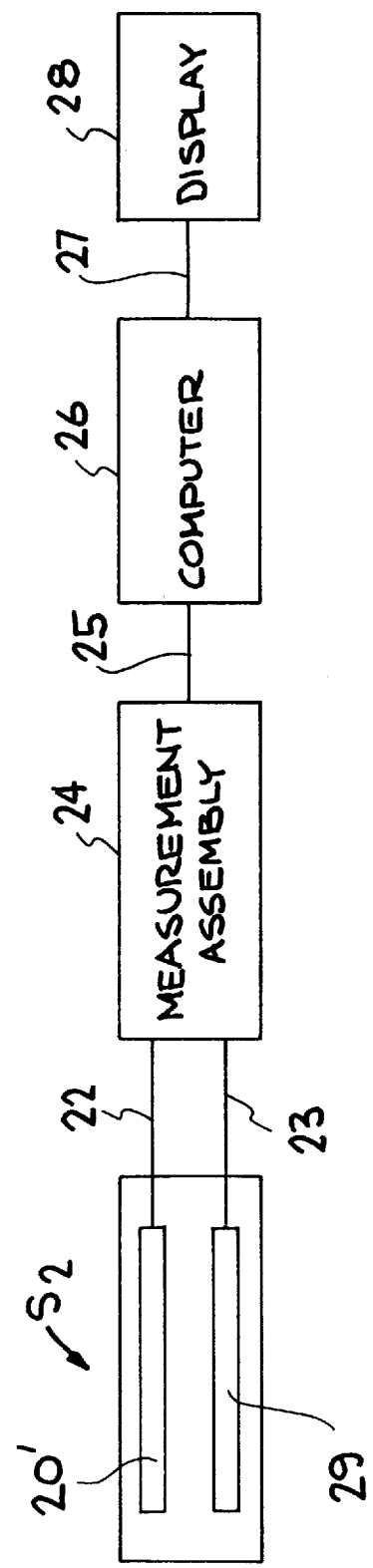
FIG. 5B illustrates the urea sensor used in conjunction with a reference sensor (a sensor without the urease coating) and appropriate electronics/computer system in order to determine the hemodialysis end point.

Both systems shown in FIGS. 5A and 5B are passive. That is, a simple potential difference is measured. The potential is measured between the sensor electrode and a real reference electrode (FIG. 5A) or between the sensor electrode and an electrode constructed similarly, only not containing the enzyme urease (FIG. 5B).

The system as illustrated in FIG. 5A comprises a monitoring sensor, generally indicated at $S_1$, composed of a urease containing sensor/electrode 20 (such as shown in FIG. 2) and a reference electrode 21, the outputs of electrodes 20 and 21 are inputted as indicated via leads 22 and 23 into a differential potential measurement electronics assembly (e.g., a pH meter, or a voltmeter with high input impedance) 24, with the output of measurement assembly 24 being inputted as indicated by lead 25 into a microcomputer 26. The microcomputer processes the data and outputs same as indicated by lead 27 to a display 28.

The system illustrated in FIG. 5B differs from that of FIG. 5A only in the construction of the monitoring sensor generally indicated at $S_2$, composed of a urease-containing sensor/electrode 20' and a similar electrode 29 constructed with all the layers of 20' only without urease in the final layer (15 of FIG. 2). The remaining components of FIG. 5B are the same as described above with respect to FIG. 5A and have been given corresponding reference numerals.

The systems of FIGS. 5A and 5B represent a completely automated form of data acquisition and display. Intermittent or continuous data acquisition can be programmed. If desired, the microcomputer 26 can be supplied with stored memory so that patient-specific information (e.g., typical values for percent reduction of urea during dialysis) can be displayed on the screen for treatment decision-making.

Figure 6A:
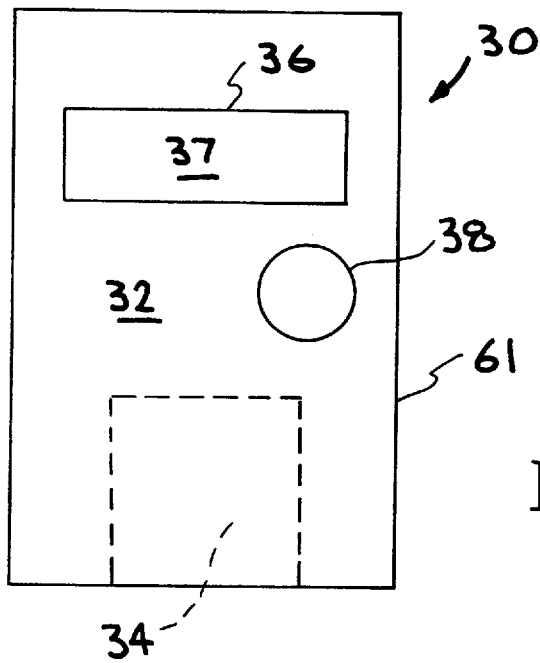
FIGS. 6A–6C illustrate an embodiment of a test device utilizing the invention.
Figure 6B:
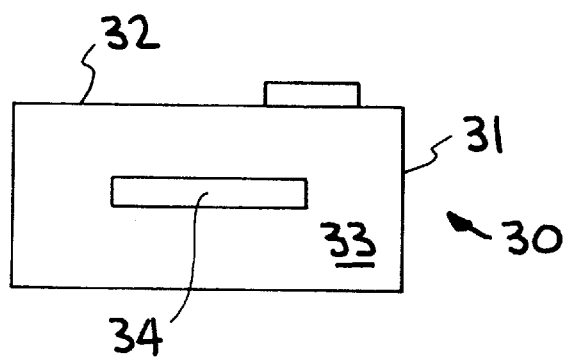
Figure 6C:
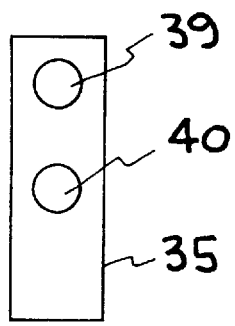

The design of the circuitry of the FIG. 5 embodiment, and potential miniaturization of the circuit components, can result in a device which can be fabricated "on a chip"

through integrated circuit manufacturing techniques, resulting in, at least, a hand-held instrument for home monitoring, such as illustrated in FIGS. 6A–6C.

FIGS. 6A–6C illustrate an embodiment of a home monitor arrangement for the use of the urea sensor for capillary blood urea monitoring. The electronics necessary to make measurement is substantially the same as that depicted in FIGS. 5A–5B, miniaturized versions of components 24–26, and, for example, the microcomputer 26 could be replaced with a microprocessor chip. In addition, initiation of measurement cycles would be provided through a push button prior to application of a blood droplet to test strip. In contrast to glucose monitors, it is expected that the urea monitor would be used semi-quantitatively as a gauge, indicating necessity for dialysis, and to schedule treatment, and not for blood urea control. Referring now to the particular embodiment of the "home" monitor illustrated in FIGS. 6A–6B, this embodiment comprises a meter generally indicated at 30, having a housing or casing 31 with a face plate 32. An end 33 of housing 31 is provided with a slot 34 to insert a test strip 35. Face plate 32 is provided with an opening 36 beneath which is a readout 37 to provide a reading of the test strip 35. An off-on button or switch 38 is positioned on face plate 32. Test strip 35 includes an electrical contact or connection section 39 adapted to contact an electrical circuit within housing 31, and a sample area or section 40 onto which a blood drop is deposited after insertion on the test strip 35 into slot 34 of housing 31. Electrical connectors (covered by inert material) run from the contact pads 39 to the test area 40. The sample area 40 essentially consist of the sensor element of FIGS. 1 and 2, which includes a coating containing urease. The substrate for the test strips can be rigid (e.g. insulated silicon or ceramic) or somewhat flexible, such as KAPTON or other plastic or reinforced material, which is sturdy enough to withstand insertion into the meter.

It has thus been shown that the present invention provides a urea biosensor for hemodialysis monitoring using a solid-state pH-sensitive electrode. The sensor element can be fabricated using known deposition technology and lends itself to mass fabrication. The sensor is based upon measurement of the pH change produced in an aqueous environment by the products of the enzyme-catalyzed hydrolysis of urea. The sensor can be used in treatment centers or as a home monitor, when used in conjunction with appropriate electronics/computer system, in order to determine the hemodialysis end point, or to determine if dialysis is necessary.

Implementation of the sensor would reduce the cost of dialysis, and other procedures where there is a need to monitor urea. Also, it would reduce exposure of medical staff to blood-bone disease, and would reduce patient discomfort and enhance overall well-being.

While a particular embodiment of a sensor element and particular embodiments utilizing the sensor element, along with specific materials, parameters etc. necessary to fabricate and utilize the invention have been set forth to exemplify and teach the principles of the invention, such are not intended to be limiting. Modifications and changes may become apparent to those skilled in the art, and it is intended that the invention be limited only by the scope of the appended claims.

The invention claimed is:

1. An electrochemical sensor adapted for detecting urea in body fluids comprising:
   a sensor element including:
      a substrate;
      a layer of metal deposited on said substrate;
      a layer of pH-sensitive oxide deposited on a portion of said layer of metal, said pH-sensitive oxide layer being wider than said metal layer and extends over at least one end of said metal layer; and
      a layer of material containing urease deposited over and covering said layer of pH-sensitive oxide.

2. The improvement of claim 1, additionally including a layer of adhesion material intermediate said substrate and said layer of metal.

3. The improvement of claim 2, wherein said layer of adhesion material is selected from the group consisting of titanium, chromium and niobium.

4. The improvement of claim 1, wherein said substrate is composed of material selected from the group consisting of alumina, insulated silicon, plastic, ceramic and glass.

5. The improvement of claim 1, wherein said layer of metal is selected from the group consisting of iridium, titanium, platinum and ruthenium, osmium, tantalum, and tungsten.

6. The improvement of claim 1, wherein said layer of pH-sensitive oxide is selected from the group consisting of $IrO_2$, $PtO_2$, $TiO_2$, $RuO_2$, $OSO_2$, $Ta_2O_5$ and $WO_3$.

7. The improvement of claim 1, wherein said layer of urease containing material composed of a coating within which said urease is physically entrapped or covalently bound.

8. The improvement of claim 1, wherein said layer of urease containing material is selected from the group consisting of polymers, copolymers, sol-gels, and cross-linked bovine serum albumin.

9. The improvement of claim 8, wherein said polymers are selected from the group consisting of poly (vinyl alcohol), polypyrrole, and polyalkylothiophenes; wherein the copolymers are selected from the group consisting of poly (vinyl alcohol), polypyrrole, polyvinyl pyridine, and polyalkylothiophenes.

10. The improvement of claim 1, wherein said layer of urease containing material contains A-b-antiurease to which urease is covalently attached.

11. A urea biosensor adapted for hemodialysis using a solid state pH electrode including:
   a sensor element comprising:
      a substrate;
      a film of adhesion material on a surface of the substrate;
      a layer of iridium on the film of said adhesion material;
      a layer of iridium oxide on at least a portion of the layer of iridium, said iridium oxide layer being wider than said iridium layer and extends over at least one end of said iridium layer; and
      a coating of urease containing material deposited over and covering the layer of iridium oxide.

12. The urea biosensor of claim 11, wherein said layer of iridium oxide extends beyond said portion of said layer of iridium.

13. The urea biosensor of claim 11, wherein said film of adhesion material has a thickness of about 500 Å, wherein said layer of iridium has a thickness of about 2000 to 4000 Å; wherein said layer of iridium oxide has a thickness of 2000–4000 Å; and wherein said coating of urease containing material has a thickness of 1 to 100 $\mu$m.

14. The urea biosensor of claim 11, wherein said layer of iridium oxide is sputter-deposited on said layer of iridium in oxygen using a target of pure iridium.

15. The urea biosensor of claim 11, wherein said coating of urease-containing material is composed of bovine serum albumin cross-linked with glutaraldehyde.

16. A method of fabricating a sensor element for a urea monitoring, comprising:

providing a substrate;

forming a metal layer on at least a portion of the substrate;

depositing a layer of pH-sensitive oxide on at least a section of the metal layer, the pH sensitive layer being wider than the metal layer and extends over at least one end of the metal layer; and forming a coating of urease containing material over said layer of pH-sensitive oxide.

17. The method of claim 16, wherein the providing of the substrate includes selecting a substrate from the group consisting of alumina, insulated silicon, ceramic, plastic and glass; wherein forming the metal layer is carried out by depositing a layer of iridium on at least a portion of the substrate; wherein depositing the layer of pH-sensitive oxide is carried out by sputter depositing in oxygen using a target of pure iridium; wherein forming the coating of urease containing material is carried out by providing a material wherein the urease is physically entrapped or covalently bound.

18. The method of claim 17, wherein the urease containing material is bovine serum albumin cross-linked with glularatdehyde containing urease with enzyme activities in the range of 25,000 to 1,000,000 units/g.

19. A system selected from the group consisting of point-of-care monitors and at-home monitors including a urea sensor element fabricated by the method of claim 16.

20. The system of claim 19, wherein the system is an at-home monitor having:

a housing;

wherein the housing includes a face plate, having an opening therein and which opening is in the form of a slot in one end of the housing;

a test strip including the urea sensor element for insertion into the slot in the housing having an electrical contact section and a sample section;

a readout means in the opening of the housing;

an off-on switch on the face plate; and an electrical circuit means within the housing adapted to be operatively connected to the off-on switch, the readout means, and the electrical contact section of the test strip.

* * * * *